United States Patent [19]

Gold et al.

[11] Patent Number: 4,470,972
[45] Date of Patent: Sep. 11, 1984

[54] 7-CARBOXYALKYLAMINOACYL-1,4-DITHIA-7-AZASPIRO[4.4]-NONANE-8-CARBOXYLIC ACIDS

[75] Inventors: Elijah H. Gold; Bernard R. Neustadt, both of West Orange; Elizabeth M. Smith, Verona, all of N.J.

[73] Assignee: Schering Corporation, Kenilworth, N.J.

[21] Appl. No.: 446,929

[22] Filed: Dec. 6, 1982

Related U.S. Application Data

[63] Continuation-in-part of Ser. No. 258,484, Apr. 28, 1981, , which is a continuation-in-part of Ser. No. 201,649, Oct. 28, 1980, abandoned, which is a continuation-in-part of Ser. No. 199,886, Oct. 23, 1980, abandoned.

[51] Int. Cl.$^3$ .................... A61K 37/00; A61K 31/40
[52] U.S. Cl. ................................................. 424/177
[58] Field of Search ................ 424/177, 274; 548/409

[56] References Cited

U.S. PATENT DOCUMENTS 4,311,697  1/1982  Krapcho ......................... 548/409
4,325,945  4/1982  Natarajan et al. ............... 548/409

Primary Examiner—Delbert R. Phillips

[57] ABSTRACT

This invention relates to 7-carboxyalkyl-aminoacyl-1,4-adithia-7-azaspiro[4.4]nonane-8-carboxylic acids. The compounds of the invention are useful in the treatment of cardiovascular disorders and especially as antihypertensive agents.

29 Claims, No Drawings

7-CARBOXYALKYLAMINOACYL-1,4-DITHIA-7-AZASPIRO[4.4]-NONANE-8-CARBOXYLIC ACIDS

This application is a continuation-in-part of U.S. Ser. No. 258,484, filed Apr. 28, 1981, which is a continuation-in-part of U.S. Ser. No. 201,649, filed Oct. 28, 1980, now abandoned, which is a continuation-in-part of U.S. Pat. No. 199,886, filed Oct. 23, 1980, now abandoned.

The present invention relates to 7-carboxyalkylaminoacyl-1,4-dithia-7-azaspiro[4.4]nonane-8-carboxylic acids. The compounds of the invention are useful in the treatment of cardiovascular disorders and especially as antihypertensive agents.

Compounds of the present invention are represented by the following formula

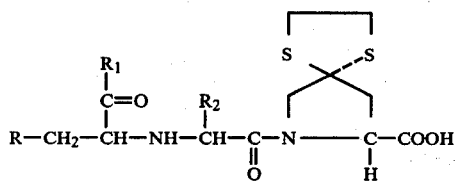

wherein:
R is lower alkyl, benzyl, benzylthio, benzyloxy, phenylthio or phenoxy;
$R_1$ is hydroxy or lower alkoxy;
$R_2$ is hydrogen, lower alkyl or amino lower alkyl;
and the pharmaceutically acceptable salts thereof.

In the above description, lower alkyl refers to straight or branched chain alkyl groups having from 1 to 6 carbon atoms, e.g. methyl, ethyl, propyl, isopropyl, butyl, pentyl, 3-methylbutyl, and hexyl, lower alkoxy refers to alkoxy groups having from 1 to 6 carbon atoms, e.g. methoxy, ethoxy, and propoxy, and amino lower alkyl refers to groups having from 1 to 6 carbon atoms, e.g. aminomethyl, aminoethyl, 3-aminopropyl and 4-aminobutyl.

In preferred compounds of formula I, $R_2$ is hydrogen, methyl or aminobutyl. Also preferred are compounds of formula I wherein $R_1$ is lower alkoxy. A third preferred group contains compounds of formula I wherein R is benzyl. More preferred are compounds of formula I wherein R is benzyl, $R_1$ is lower alkoxy and $R_2$ is methyl. Most preferred are compounds wherein R is benzyl, $R_1$ is ethoxy and $R_2$ is methyl.

Preferred compounds of the invention are 7-[N-(1(S)-carboethoxy-3-phenylpropyl)-(S)-alanyl]-1,4-dithia-7-azaspiro[4.4]nonane-8(S)-carboxylic acid, 7-[Nα-(1(S)-carboethoxy-3-phenylpropyl)-(S)-lysyl]-1,4-dithia-7-azaspiro[4.4]nonane-8(S)-carboxylic acid and 7-[Nα-(1(S)-carboxy-3-phenylpropyl)-(S)-lysyl]-1,4-dithia-7-azaspiro[4.4]nonane-8(S)-carboxylic acid.

The compounds of the present invention can be produced by various methods and subroutes, one of which is depicted in the following equations. Additional methods may be found in European Patent Application No. 50,800, filed Oct. 15, 1981 and published May 5, 1982. Reactive groups not involved in the condensations described below such as amino, carboxy, mercapto, etc., may be protected by methods standard in peptide chemistry prior to the coupling reactions and subsequently deprotected to obtain the desired products. For example, if $R_1$ is alkoxy or protected by a carboxy protecting group such as benzyloxy, it can be converted by well known methods such as hydrolysis or hydrogenation to I, wherein $R_1$ is hydroxy. Such reactions are demonstrated in the Examples.

Compounds of the present invention are prepared as follows:

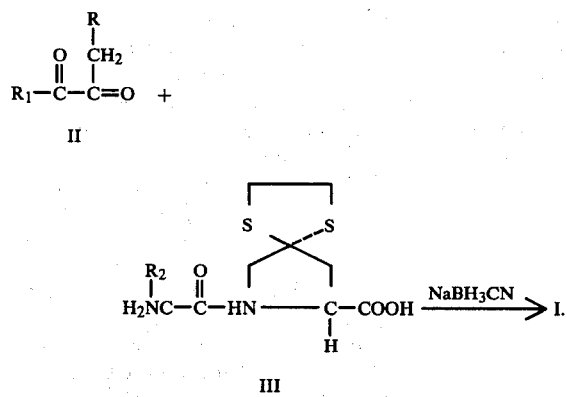

Keto acid (or ester) II is condensed with dipeptide III in aqueous solution, optimally near neutrality, or in a suitable organic solvent (for example, $CH_3OH$) in the presence of sodium cyanoborohydride to give I. Alternatively, the intermediate Schiff base, enamine, or aminol may be catalytically reduced to yield product I, for example, by hydrogen in the presence of palladium black. The ratio of diasteriomeric products formed may be altered by choice of catalyst.

Alternatively II can be condensed with an amino acid IV

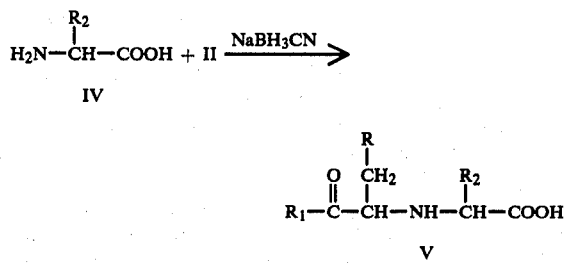

under the same conditions to yield amino acid V. Subsequent coupling by known methods with amino acid derivative VI gives I.

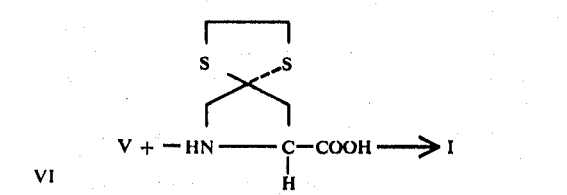

The known methods encompass reactive group protection during the coupling reaction, for example, by N-formyl, N-t-butoxycarbonyl and N-carbobenzyloxy groups followed by their removal to yield I. Furthermore, if desired, the carboxylic acid function in VI may be protected by removable ester groups such as benzyl, ethyl, t-butyl, and the like. Condensing agents in this synthetic route are typically those useful in peptide chemistry such as dicyclohexylcarbodiimide (DCC) or diphenylphosphoryl azide (DPPA) or V may be activated via the intermediacy of active esters such as that derived from N-hydroxysuccinimide, 1-hydroxybenzotriazole, and the like.

As desired, protecting groups may be removed by known methods.

The starting materials which are required for the above processes herein described are known in the literature or can be made by known methods.

In the compounds of the formula I, the carbon atoms to which R—CH$_2$— and R$_2$— (where R$_2$ is not hydrogen) are attached and the carbon at the 8-position of the 1,4-dithia-7-azaspiro[4.4]nonane ring are asymmetric. The compounds accordingly exist in diastereoisomeric forms or in mixtures thereof. The above described synthesis can utilize racemates, enantiomers or diastereomers as starting materials. Enantiomeric intermediates may be obtained by resolution methods known in the art. When diastereomeric products result from the synthetic procedures, the diastereomeric products can be separated by conventional chromatographic or fractional crystallization methods.

In general, the amino acid part-structures, i.e.,

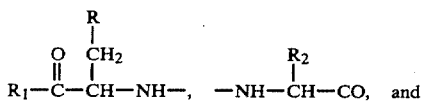

of formula I are preferred in the configuration analogous to that of natural L-amino acids. Usually, natural L-amino acids are assigned the S-configuration. A notable exception is the natural amino acid L-cysteine which is assigned the R-configuration.

The compounds of this invention form salts with various inorganic and organic acids and bases which salts are also within the scope of the invention. Such salts include ammonium salts, alkali metal salts, e.g. sodium and potassium salts, and alkaline earth metal salts, e.g. calcium and magnesium salts. Salts with organic and inorganic acids may be prepared, e.g., HCl, HBr, H$_2$SO$_4$, H$_3$PO$_4$, methanesulfonic acid, toluenesulfonic acid, maleic acid, fumaric acid and camphorsulfonic acid. The non-toxic physiologically acceptable salts are preferred, although other salts are also useful, e.g., in isolating or purifying the product. Especially preferred acid salts are the hydrochloride and the hemimaleate.

The salts may be formed by conventional means, as by reacting the free acid or base forms of the product with one or more equivalents of the appropriate base or acid in a solvent or medium in which the salt is insoluble, or in a solvent such as water which is then removed in vacuo, by freeze-drying, or by exchanging the cations of an existing salt for another cation on a suitable ion exchange resin.

The following examples illustrate the preparation of the compounds of the present invention. The diastereomers prepared as set forth below may be isolated by column chromatography or by fractional crystallization.

EXAMPLE 1

7-[N-(1-Carboethoxy-3-phenylpropyl)-(S)-alanyl]-1,4-dithia-7-azaspiro[4.4]nonane-8(S)-carboxylic acid A. Dissolve 7.0 g of 1-benzyloxycarbonyl-4-keto-(S)-proline methyl ester in 75 ml of glacial acetic acid. Add 0.7 g of p-toluenesulfonic acid and 2.8 g of 1,2-ethanedithiol and heat under reflux with stirring for eighteen hours. Add the reaction mixture to saturated sodium bicarbonate solution and extract with ethyl acetate. Dry the organic layer over magnesium sulfate and concentrate it. Place the residue on a column of silica gel (300 g, 60–200 mesh) and elute with hexane:ethyl acetate (1:1) to give 7-benzyloxycarbonyl-1,4-dithia-7-azaspiro[4.4]nonane-8(S)-carboxylic acid methylester, a yellow oil having $[\alpha]_D^{26}$ −12.6° (dioxane).

B. Dissolve 3.0 g of 7-benzyloxycarbonyl-1,4-dithia-7-azaspiro[4.4]nonane-8(S)-carboxylic acid methyl ester (3.0 g) in 20 ml of 20% hydrobromic acid in glacial acetic acid and stir the mixture at room temperature for two hours. Add the mixture dropwise to diethyl ether at 0°–5° to give 1,4-dithia-7-azaspiro[4.4]nonane-8(S)-carboxylic acid methyl ester hydrobromide, a brown solid m.g. 156°–158°.

C. Dissolve the 1,4-dithia-7-azaspiro[4.4]nonane-8(S)-carboxylic acid methyl ester hydrobromide from paragraph B in 0.1 N NaOH and extract with ethyl acetate. Dry the organic layer over magnesium sulfate and concentrate in vacuo to give 1,4-dithia-7-azaspiro[4.4]nonane-8(S)-carboxylic acid methyl ester (1.35 g). Dissolve the latter in 100 ml of ethyl acetate and treat with 2.07 g of N-benzyloxycarbonyl-(S)-alanine, N-hydroxysuccinimide ester. Stir the reaction mixture at room temperature for eighteen hours and concentrate in vacuo. Place the residue on a column of silica gel (300 g, 60–200 mesh) and elute with hexane:ethyl acetate 4:1 to obtain 7-[N-benzyloxycarbonyl-(S)-alanyl]-1,4-dithia-7-azaspiro[4.4]nonane-8(S)-carboxylic acid, methyl ester, a yellow oil $[\alpha]_D^{26}$ = −14.8° (ethanol).

D. Dissolve 1.05 g of 7-[N-benzyloxycarbonyl(S)-alanyl]-1,4-dithia-7-azaspiro[4.4]nonane-8(S)-carboxylic acid, methyl ester in 100 ml of methanol. Add 10 ml of 2.5 N sodium hydroxide and stir the mixture at room temperature for sixteen hours. Concentrate the mixture under nitrogen, dissolve the oil in 0.1 N sodium hydroxide and dilute with ice water. Adjust to pH2 with concentrated hydrochloric acid, then extract with ethyl acetate. Dry the organic phase over magnesium sulfate and concentrate it. Place the residue on a column of silica gel (100 g, 60–200 mesh) and elute with chloroform:glacial acetic acid 19:1 to obtain 7-[N-benzyloxycarbonyl-(S)-alanyl]-1,4-dithia-7-azaspiro[4.4]nonane-8(S)-carboxylic acid, $[\alpha]_D^{26}$ = −15.8° (ethanol).

E. Dissolve 1.4 g of 7-[N-benzyloxycarbonyl-(S)-alanyl]-1,4-dithia-7-azaspiro[4.4]nonane-8(S)-carboxylic acid in 20 ml of 20% hydrobromic acid in glacial acetic acid and stir the mixture at room temperature for two hours. Add the mixture dropwise to diethyl ether at 0°–5° C. to give 7-[(S)-alanyl]-1,4-dithia-7-azaspiro[4.4]nonane-8(S)-carboxylic acid hydrobromide which is used immediately in the process described in paragraph F below.

F. Dissolve the 7-[(S)-alanyl]-1,4-dithia-7-azaspiro[4.4]nonane-8(S)-carboxylic acid hydrobromide (prepared in paragraph E next above) in 100 ml of absolute methanol. Add 0.5 g of 2-oxo-4-phenylbutyric acid, ethyl ester and 10 ml of 3A molecular sieve pellets and

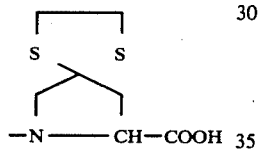

stir the mixture at room temperature for eighteen hours. Filter the reaction mixture and treat the filtrate with 0.30 g of sodium cyanoborohydride at room temperature for two hours. Concentrate the mixture under nitrogen and dilute the oil with 5% hydrochloric acid to pH 2 to 4 and stir at room temperature for one hour. Adjust the pH of the solution to pH 8 with 2.5 N sodium hydroxide solution and absorb the solution in 150 ml of XAD-2 resin. Elute the resin with 800 ml of water and then with 800 ml of methanol. Concentrate the methanol solution, place the residue on a column of silca gel (100 g, 60-200 mesh) and elute with chloroform:isopropanol:7% ammonium hydroxide 1:1:1 (organic layer) to obtain 7-[N-(1-carboethoxy-3-phenylpropyl)-(S)-alanyl]-1,4-dithia-7-azaspiro[4.4]nonane-8(S)-carboxylic acid, a white solid, m.p. 56°-60° C., $[\alpha]_D^{26} -25.5°$ (ethanol).

EXAMPLE 2

7-[N-(1-Carboxy-3-phenylpropyl)-(S)-alanyl]-1,4-dithia-7-azaspiro[4.4]nonane-8(S)-carboxylic acid Hydrolyze 0.18 of the product of Example 1 in 20 ml of methanol with 1.3 ml of 2.5 N sodium hydroxide for 20 hours at room temperature. Concentrate the reaction mixture in vacuo at room temperature. Dissolve the resultant residue in water and place on Bio Rad AG-50W-X2 (100-200 mesh) resin in the hydrogen form. Elute with water (300 ml), then with 2% pyridine in water. Concentrate the desired eluant fractions to obtain the title compound.

EXAMPLE 3

7-[N-(1(S)-Carboethoxy-3-phenylpropyl)-(S)-alanyl]-1,4-dithia-7-azaspiro[4.4]nonane-8(S)-carboxylic acid A. Dissolve 1-benzyloxycarbonyl-4-keto-(S)-proline (15.7 g, 60 mmol) in acetic acid (45 ml) and ethyl acetate (45 ml), add 1,2-ethanedithiol (6.2 g, 66 mmol) and stir under nitrogen. Add boron trifluoride etherate (redistilled) and stir 4 hours. Pour the reaction mixture into a mixture of water (175 ml) ethyl acetate (120 ml) and ether (60 ml). Wash the organic layer with water (3×175 ml) then extract twice with 1.0 N sodium bicarbonate (150 ml, then 50 ml). Acidify the aqueous layer to pH 1 with concentrated hydrochloric acid, extract twice with ether (150 ml, then 50 ml). Wash the organic layer with brine, dry over anhydrous magnesium sulfate and concentrate in vacuo to obtain crude 7-benzyloxycarbonyl-1,4-dithia-7-azaspiro[4.4]nonane-8(S)-carboxylic acid as an oil (16.1 g).

B. Dissolve the product of Step A in acetic acid (30 ml) by stirring under nitrogen. Add 23% hydrobromic acid in acetic acid (50 ml), stir 3 hours and dilute over 5 minutes with ether (320 ml). Filter the solid, wash twice with ether (2×150 ml) and air dry to obtain a purple powder.

Dissolve the crude product in boiling ethanol (120 ml), add Darco grade 6-60 (6 g), and filter hot, washing with 2×10 ml hot ethanol. Dilute the filtrate with ether (300 ml) and allow to stand one hour. Filter the resultant precipitate, wash with ether (2×50 ml), and air dry to give 1,4-dithia-7-azaspiro[4.4]nonane-8(S)-carboxylic acid hydrobromide as beige crystals.

C. (1)a. To a 5 L flask equipped with a magnetic stirrer, dropping funnel and nitrogen inlet tube, add a solution of 190 g (0.92 mole) of S-alanine benzyl ester p-toluenesulfonate and 258 g (0.734 mole) of 2-oxo-4-phenyl butanoate in 1.4 L of ethanol. Stir for 2 hours under nitrogen. Add a solution of 17.7 g (0.282 mole) of sodium cyanoborohydride in 550 mL of ethanol, with stirring, over 90 minutes. Stir the solution overnight and concentrate to dryness in vacuo at room temperature. Partition the residue between 500 mL of H$_2$O and 2 L of ether. Dry the ether layer over MgSO$_4$ and filter. Add 1.3 M ethereal HCl to pH 4. Remove the ether and excess HCl in vacuo at room temperature. Slurry the residue in 250 mL of ether and dilute with 750 mL of hexane. Decant the supernatent from the resulting precipitate and wash with two 300 mL portions of ether. Triturate the residue with 300 mL of ether and filter under N$_2$ to give 134 g of a white solid. Slurry the solid in ether and make basic with saturated aqueous NaHCO$_3$. Dry the organic layer over MgSO$_4$, filter and concentrate in vacuo at room temperature to give 135 g of N-(1-carboethoxy-3-phenylpropyl)-(S)-alanine benzyl ester as an amber oil.

Dissolve 135 g of the resultant amber oil in 510 ml of ethyl acetate and add a hot solution of 40.5 g maleic acid in 895 ml of ethyl acetate. Cool to room temperature, filter the resulting precipitate, and recrystallize the precipitate from ethyl acetate to give N-(1(S)-carboethoxy-3-phenylpropyl)-(S)-alanine benzyl ester hemimaleate as a white solid, m.p. 127°-128° C., $[\alpha]_D^{26}=0°$ (H$_2$O).

Slurry 7.0 g (0.015 mole) of the above product in ethyl acetate and adjust to pH 8 with saturated aqueous sodium bicarbonate. Wash the organic layer with saturated aqueous sodium chloride solution, dry over magnesium sulfate, filter, and concentrate in vacuo at room temperature to a colorless oil. Dissolve the resultant oil in 100 ml ethanol containing 0.7 g of 10% Pd/C and hydrogenate at 60 psi at room temperature for 2 hours. Filter and evaporate the solvent under vacuum at room temperature to obtain 4.0 g of N-(1(S)-carboethoxy-3-phenylpropyl)-(S)-alanine as a white solid, m.p. 147°-148° C., $[\alpha]_D^{26}+24.8°$ (methanol).

b. To a solution of the product of Step (1)a (8.93 g, 32 mmol) and N-hydroxysuccinimide (4.42 g, 38.4 mmol) in dry dimethylformamide (64 ml), add 1-(3-dimethylaminopropyl)-3-ethylcarbodiimide hydrochloride (7.3 g, 38.4 mmol) and stir for 12 hours. Pour the reaction mixture into ethyl acetate (320 ml), wash with water (100 ml), brine (100 ml), and dry the organic layer over anhydrous magnesium sulfate. Concentrate in vacuo to obtain N-[1(S)-ethoxycarbonyl-3-phenylpropyl]-(S)-alanine succinimidyl ester as an oil.

(2) Dissolve the product of Step (1)b and 1,4-dithia-7-azaspiro[4.4]nonane-8(S)-carboxylic acid hydrobromide (Step B) (9.16 g, 32 mmol) in dimethylformamide (155 ml) and cool to 0°-5° C. Add triethylamine (8.9 ml, 64 mmol) dropwise over 5 minutes, and rinse the funnel with dimethylformamide (5 ml). Stir at room temperature for 16 hours, concentrate in vacuo to 50 ml and dilute with water (150 ml). Adjust the solution to pH 4.0 with 1 N hydrochloric acid. Extract the resultant brown gum with ethyl acetate (4×100 ml), combine the extracts, wash with water (20 ml) then brine (20 ml) and dry the organic phase over anhydrous magnesium sulfate. Evaporate the solvent in vacuo to obtain the title compound as a brown oil.

To purify, dissolve the crude product (3.3 g) in methanol (10 ml), place on Sephadex LH-20 (2.5×55 cm column) and elute with methanol. Combine the desired fractions and evaporate the solvent in vacuo to give the title compound as a solid white foam. Analytically pure material has an $[\alpha]_D^{26}= -29.5°$ (ethanol).

EXAMPLE 4

7-[N-(1(S)-Ethoxycarbonyl-3-phenylpropyl)-(S)-alanyl]-1,4-dithia-7-azaspiro[4.4]nonane-8(S)-carboxylic acid hydrochloride Dissolve the crude product of Example 3, Step C (27 g, 5.8 mmol) in acetonitrile (18 ml), add concentrated hydrochloric acid (0.5 ml, 6 mmol) and seed. After crystallization starts, refrigerate for 10 hours. Collect the crystals, wash with cold acetonitrile, then ether, and let dry to give crystals, m.p. 176°–178° C. (dec.).

To recrystallize the above product, dissolve the crystals (0.5 g) in hot methanol (1 ml), dilute with acetonitrile (5 ml) and seed. Refrigerate for 10 hours, collect the crystals and let dry to obtain the title compound, m.p. 176°–178° C., $[\alpha]_D^{26} = -11.2°$ (ethanol) (analytically pure material).

EXAMPLE 5

7-[N-(1(S)-Ethoxycarbonyl-3-phenylpropyl)-(S)-alanyl]-1,4-dithia-7-azaspiro[4.4]nonane-8(S)-carboxylic acid hemimaleate Dissolve the crude product of Example 3, Step C (2.9 g, 5.2 mmol) and maleic acid (0.7 g, 60 mmol) in hot acetonitrile (18 ml) and refrigerate for 10 hours. Collect the crystals, wash with cold acetonitrile and let dry to obtain the title compound as tan crystals (1.6 g). Analytically pure material has m.p. 124°–126° C., $[\alpha]_D^{26} = -14.3°$ (ethanol).

EXAMPLE 6

7-[N-(1(S)-Carboxy-3-phenylpropyl)-(S)-alanyl]-1,4-dithia-7-azaspiro[4.4]nonane-8(S)-carboxylic acid As described in Example 2, hydrolyze the product of Example 3 (0.3 g) in methanol (30 ml) with 2.5 N sodium hydroxide (2.0 ml) to give the title compound, m.p. 115°–117° C., $[\alpha]_D^{26} = -2.4°$ (H$_2$O); +1.9° (ethanol).

EXAMPLE 7

7-[N-(1-Carboethoxy-3-phenylpropyl)glycyl]-1,4-dithia-7-azaspiro[4.4]nonane-8(S)-carboxylic acid A. As described in Example 1, react 1-benzyloxycarbonyl-4-keto-(S)-proline, ethyl ester (prepared from the acid by esterification in ethanol) with 1,2-ethane dithiol to obtain 7-benzyloxycarbonyl-1,4-dithia-7-azaspiro[4.4]nonane-8(S)-carboxylic acid, ethyl ester, a yellow oil $[\alpha]_D^{26} - 21.0°$ (ethanol).

B. Convert 2.22 g of 7-benzyloxycarbonyl-1,4-dithia-7-azaspiro[4.4]nonane-8(S)-carboxylic acid, ethyl ester (prepared as described in paragraph A) to 1,4-dithia-7-azaspiro[4.4]nonane-8(S)-carboxylic acid, ethyl ester as described in Example 1 and couple this compound with 1.5 g of N-benzyloxycarbonylglycine, N-hydroxysuccinimide ester as described in Example 2 to yield 7-(N-benzyloxycarbonylglycyl)-1,4-dithia-7-azaspiro[4.4]nonane-8(S)-carboxylic acid, ethyl ester, a yellow oil $[\alpha]_D^{24} - 15.9°$. (ethanol).

C. Hydrolyze 1.43 g of 7-(N-benzyloxycarbonylglycyl)-1,4-dithia-7-azaspiro[4.4]nonane-8(S)-carboxylic acid, ethyl ester (prepared as described in paragraph B next above) with sodium hydroxide as described in Example 1D to obtain 7-(N-benzyloxycarbonylglycyl)-1,4-dithia-7-azaspiro[4.4]nonane-8(S)-carboxylic acid, a colorless oil, $[\alpha]_D^{26} - 7.9°$ (ethanol).

D. Treat 0.95 of the acid obtained in the process described in paragraph C next above with 20% hydrobromic acid in glacial acetic acid as described in Example 1E to obtain 7-glycyl-1,4-dithia-7-azaspiro[4.4]nonane-8(S)-carboxylic acid, hydrobromide, $[\alpha]_D^{26} - 18.7°$ (ethanol).

E. As described in Example 1F, couple 0.76 g of 7-glycyl-1,4-dithia-7-azaspiro[4.4]nonane-8(S)-carboxylic acid, hydrobromide (prepared as described in paragraph D next above) with 0.50 g of 2-oxo-4-phenylbutyric acid, ethyl ester to obtain 7-[N-(1-carboethoxy-3-phenylpropyl)glycyl]-1,4-dithia-7-azaspiro[4.4]nonane-8(S)-carboxylic acid $[\alpha]_D^{26} - 39.0°$ (ethanol).

EXAMPLE 8

7-[N-(1-Carboxy-3-phenylpropyl)glycyl]-1,4-dithia-7-azaspiro[4.4]nonane-8(S)-carboxylic acid As described in Example 2, hydrolyze 7-[N-(1-carboethoxy-3-phenylpropyl)glycyl]-1,4-dithia-7-azaspiro[4.4]nonane-8(S)-carboxylic acid (prepared as described in Example 2) with sodium hydroxide to give the title compound.

In a similar manner, using suitable reagents, prepare the following compounds:

7-[N-(1(S)-carbomethoxy-3-phenylpropyl)-(S)-alanyl]-1,4-dithia-7-azaspiro[4.4]nonane-8(S)-carboxylic acid;

7-[N-(1(R)-carboethoxy-2-benzylthioethyl)-(S)-alanyl]-1,4-dithia-7-azaspiro[4.4]nonane-8(S)-carboxylic acid;

7-[N-(1(S)-carboethoxy-2-phenoxyethyl)-(S)-alanyl]-1,4-dithia-7-azaspiro[4.4]nonane-8(S)-carboxylic acid;

7-[Nα-(1(S)-carboethoxy-3-phenylpropyl)-(S)-lysyl]-1,4-dithia-7-azaspiro[4.4]nonane-8(S)-carboxylic acid;

7-[Nα-(1(S)-carboxy-3-phenylpropyl)-(S)-lysyl]-1,4-dithia-7-azaspiro[4.4]nonane-8(S)-carboxylic acid;

7-[N-(1(R)-carboethoxy-2-phenylthioethyl)-(S)-alanyl]-1,4-dithia-7-azaspiro[4.4]nonane-8(S)-carboxylic acid; and 7-[N-(1(S)-carboethoxy-2-benzyloxyethyl)-(S)-alanyl]-1,4-dithia-7-azaspiro[4.4]nonane-8(S)-carboxylic acid;

7-[N-(1(S)-carboethoxypentyl)-(S)-alanyl]-1,4-dithia-7-azaspiro[4.4]nonane-8(S)-carboxylic acid;

7-[N-(1(S)-carboethoxybutyl)-(S)-alanyl]-1,4-dithia-7-azaspiro[4.4]nonane-8(S)-carboxylic acid; and 7-[N-(1(S)-carboethoxyhexyl)-(S)-alanyl]-1,4-dithia-7-azaspiro[4.4]nonane-8(S)-carboxylic acid.

The compounds of this invention are useful in view of their pharmacological properties. In particular, they possess activity as antihypertensive agents as evidenced by their ability to reduce blood pressure in mammals in which the blood pressure has become abnormally elevated.

The compounds of the present invention can be combined with pharmaceutical carriers and administered in a variety of well known pharmaceutical forms suitable for oral or parenteral administration to provide compositions useful in the treatment of cardiovascular disorders and particularly mammalian hypertension.

The effective daily antihypertensive dose (ED$_{50}$) of the compounds of this invention will typically be in the range of about 0.1 to about 10 mg/kg, of mammalian weight, administered in single or divided doses. The exact dose to be administered is dependent upon where the particular compound lies within the above quoted range, as well as upon the age, weight and condition of the individual.

Generally, in treating humans having hypertension, the compounds of this invention may be administered to patients in need of such treatment in a dose range of 5 to 150 mg per patient generally given twice daily, thus giving a total daily dose of from 10 to 300 mg per day. Also, the compounds of this invention may be given in combination with diuretics or other antihypertensives. Typically, these are combinations whose individual per day dosages range from one-fifth of the minimally recommended clinical dosages to the maximum recommended levels for the entities when they are given singly. Examples of such diuretics or other antihypertensives are hydrochlorothiazide, chlorothiazide, ethacrynic acid, amiloride, furosemide, propranolol, timolol and methyldopa.

The antihypertensive compositions containing the compounds of this invention will preferably contain from about 5 to about 250 mg of the active compound per dosage unit.

Since the compounds of the present invention are believed to act as angiotensin converting enzyme inhibitors, it is also contemplated that they may be used in treating other cardiovascular disorders, for example congestive heart failure, in the same manner as other ACE inhibitors such as captopril and MK-421 may be used.

The compositions of the present invention are most preferably administered orally. Typical formulations for oral administration are those such as tablets, capsules, syrups, elixirs or suspensions. Typical injectable formulations include solutions and suspensions.

Typical acceptable pharmaceutical carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tri-calcium phosphate; sodium sulfate; calcium sulfate, polyvinylpyrrolidone, polyvinyl alcohol; stearate acid; alkaline earth metal stearates such as magnesium stearate and calcium stearate, stearate acid vegetable oils such as peanut oil, cottonseed oil, sesame oil, olive oil and corn oil; non-ionic, cationic and anionic surfactants; ethylene gylcol polymers; beta-cyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

The following example describes in detail a composition that is illustrative of the present invention. It will be apparent to those skilled in the art that many modifications, both of materials and methods, may be practiced without departing from the purpose and intent of this disclosure.

In the following example, the active ingredient is 7-[N-(1(S)-carboethoxy-3-phenylpropyl)-(S)-alanyl]-1,4-dithia-7-azaspiro[4.4]nonane-8(S)-carboxylic acid hydrochloride, though any of the compounds of the invention may be similarly formulated.

EXAMPLE 9

| Tablet | Amount (mg) |
| --- | --- |
| Active Ingredient | 75.0 |
| Lactose | 80.5 |
| Corn Starch | 6.0 |
| Water (per thousand tablets) | 60 ml (evaporates) |
| Corn starch | 37.5 |
| Magnesium Stearate | 1.0 |
|  | 200.0 |

Blend the active ingredient with the lactose until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

We claim:

1. A compound represented by the formula $$R-CH_2-CH(C(=O)R_1)-NH-CH(R_2)-C(=O)-N\underset{H}{\overset{S\diagup\diagdown S}{\diagdown\diagup}}C-COOH$$

wherein:
R is a lower alkyl, benzyl, benzylthio, benzyloxy, phenylthio, or phenoxy;
$R_1$ is hydroxy or lower alkoxy;
$R_2$ is hydrogen, lower alkyl or aminoloweralkyl;
and the pharmaceutically acceptable salts thereof.

2. A compound of claim 1 wherein $R_2$ is methyl.

3. A compound of claim 2 wherein $R_1$ is lower alkoxy.

4. A compound of claim 3 wherein R is benzyl.

5. A compound of claim 4 wherein $R_1$ is ethoxy.

6. A compound of claim 5 which is 7-[N-(1(S)-carboethoxy-3-phenylpropyl)-(S)-alanyl]-1,4-dithia-7-azaspiro[4.4]-nonane-8(S)-carboxylic acid hydrochloride.

7. A compound of claim 2 which is 7-[N-(1(S)-carboxy-3-phenylpropyl)-(S)-alanyl]-1,4-dithia-7-azaspiro[4.4]-nonane-8(S)-carboxylic acid hydrochloride.

8. A compound of claim 2 which is 7-[N-(1(S)-carboxy-3-phenylpropyl)-(S)-alanyl]-1,4-dithia-7-azaspiro[4.4]-nonane-8(S)-carboxylic acid.

9. A compound of claim 5 which is 7-[N-(1(S)-carboethoxy-3-phenylpropyl)-(S)-alanyl]-1,4-dithia-7-azaspiro[4.4]-nonane-8(S)-carboxylic acid hemimaleate.

10. A compound of claim 1 wherein $R_2$ is hydrogen.

11. A compound of claim 1 wherein $R_2$ is aminobutyl.

12. A compound of claim 11 which is 7-[Nα-(1(S)-carboethoxy-3-phenylpropyl)-(S)-lysyl]-1,4-dithia-7-azaspiro[4.4]nonane-8(S)-carboxylic acid dihydrochloride.

13. A compound of claim 11 which is 7-[Nα-(1(S)-carboethoxy-3-phenylpropyl)-(S)-lysyl]-1,4-dithia-7-azaspiro[4.4]nonane-8(S)-carboxylic acid.

14. A compound of claim 11 which is 7-[Nα-(1(S)-carboxy-3-phenylpropyl)-(S)-lysyl]-1,4-dithia-7-azaspiro[4.4]nonane-8(S)-carboxylic acid dihydrochloride.

15. A compound of claim 11 which is 7-[Nα-(1(S)-carboxy-3-phenylpropyl)-(S)-lysyl]-1,4-dithia-7-azaspiro[4.4]nonane-8(S)-carboxylic acid.

16. A compound of claim 1 wherein R is benzylthio.

17. A compound of claim 1 wherein R is benzyloxy.

18. A compound of claim 1 wherein R is phenylthio.

19. A compound of claim 1 wherein R is phenyloxy.

20. A compound of claim 1 wherein R is lower alkyl.

21. A compound of claim 20 which is 7-[N-(1(S)-carboethoxypentyl)-(S)-alanyl]-1,4-dithia-7-azaspiro [4.4]-nonane-8(S)-carboxylic acid hydrochloride.

22. A compound of claim 20 which is 7-[N-(1(S)-carboethoxybutyl)-(S)-alanyl]-1,4-dithia-7-azaspiro[4.4]-nonane-8(S)-carboxylic acid hydrochloride.

23. A compound of claim 20 which is 7-[N-(1(S)-carboethoxyhexyl)-(S)-alanyl]-1,4-dithia-7-azaspiro [4.4]-nonane-8(S)-carboxylic acid hydrochloride.

24. A compound of claim 1 wherein the pharmaceutically acceptable salts is an acid salt.

25. A compound of claim 24 wherein the acid salt is hydrochloride or hemimaleate.

26. A pharmaceutical composition comprising an antihypertensive effective amount of a compound according to claim 1 together with a pharmaceutically acceptable carrier.

27. A pharmaceutical composition comprising an antihypertensive effective amount of a compound according to claim 6 together with a pharmaceutically acceptable carrier.

28. A method of treating hypertension in mammals comprising administering to a mammal afflicted with hypertension an effective amount of a compound according to claim 1.

29. A method of treating hypertension in mammals comprising administering to a mammal afflicted with hypertension an effective amount of a compound according to claim 6.

* * * * *

UNITED STATES PATENT AND TRADEMARK OFFICE

CERTIFICATE EXTENDING PATENT TERM
UNDER 35 U.S.C. § 156

PATENT NO.      : 4,470,972

ISSUED          : September 11, 1984

INVENTOR(S)     : Elijah H. Gold et al.

PATENT OWNER    : Schering Corporation

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

TWO YEARS from the original expiration date of the patent, September 11, 2001, with all rights pertaining thereto as provided by 35 U.S.C. § 156(b).

I have caused the seal of the Patent and Trademark Office to be affixed this 31st day of May 1996.

Bruce A. Lehman
Assistant Secretary of Commerce and
Commissioner of Patents and Trademarks